US00PP09196P

United States Patent [19]

Lamb et al.

[11] Patent Number: Plant 9,196

[45] Date of Patent: Jul. 11, 1995

[54] ANTHURIUM PLANT NAMED 'BUBBLE GUM'

[75] Inventors: Ann E. Lamb; Robert D. Hartman, both of Lake Placid, Fla.

[73] Assignee: Twyford International, Inc., Sebring, Fla.

[21] Appl. No.: 223,047

[22] Filed: Apr. 5, 1994

[51] Int. Cl.[6] ..... A01H 5/00

[52] U.S. Cl. ..... Plt./88.1

[58] Field of Search ..... Plt. 88.1

*Primary Examiner*—James R. Feyrer

*Attorney, Agent, or Firm*—Foley & Lardner

[57] ABSTRACT

An Anthurium plant named Bubble Gum characterized by its flat rounded pink spathes which are held above the foliage, compact branched habit, and wide, leathery, dark green, glossy leaves.

2 Drawing Sheets

The present invention comprises a new and distinct cultivar of Anthurium, botanically known as Anthurium hybrid, and referred to by the cultivar name Bubble Gum.

The new cultivar is a product of a breeding program carried out by the inventors Ann E. Lamb and Robert D. Hartman. The seedling is a result of a cross of unknown parentage made by the inventors in Palmdale, Fla. The cultivar was discovered from the progeny of the stated cross in Palmdale, Fla. by Ann E. Lamb. Tissue culture performed by Ann E. Lamb in Palmdale, Fla. was used to increase the number of plants for evaluation and has demonstrated the stability of the combination of characteristics of Bubble Gum from generation to generation. The parents are proprietary cultivars used in the breeding program.

The following observations, measurements and values describe plants grown in Homestead, Fla. under shadehouse conditions which closely approximate those generally used in horticultural practice.

The following traits have been repeatedly observed to be characteristics which in combination distinguish Bubble Gum as a unique new cultivar.

1. The plant produces flat, somewhat round medium pink spathes which are long lasting.

2. The flowers are held upright above and among the foliage.

3. The leaves are wide, leathery, very dark green, durable, and have a shiny surface.

4. The plant habit is branched and compact.

All color references are measured against The Royal Horticultural Society color chart. Colors are approximate as color depends on horticultural practices such as light level and fertilization rate, among others, without, however, any change in genotype.

In color photographic drawings the photograph on sheet 1 comprises a top perspective view of the inflorescence and foliage of a plant of Bubble Gum in a 15.5 cm pot. The photograph on sheet 2 illustrates the flowers and foliage in greater detail.

the photographs were taken approximately 24 weeks after planting a 20 week old liner obtained by tissue culture and grown under appropriate growing conditions. Colors are as accurate as possible with color illustrations of this type.

Classification: Anthurium hybrid, cv, Bubble Gum.

Origin: Seedling of unknown parentage.

Propagation: Asexual production either by tissue culture or division.

Plant: A 20 week old liner grown in a 15.5 cm pot for 24 weeks under appropriate growing conditions, will reach a mature size of approximately 26 cm. to 34 cm. in height and approximately 37 cm to 48 cm. in width.

Leaves:

*Form.*—The leaf blade is ovate with a cuspidate tip and a cordate base. The margins are entire. The midrib is straight over the length of the leaf. The leaf blade tends to be flat over the width of the leaf. The leaf margin is straight.

*Size.*—Leaf blades of a mature sized plant are approximately 16 cm to 19 cm in length and approximately 11 cm to 13 cm in width.

*Petiole.*—The petiole is approximately 23.2 cm to 26.5 cm in height from the base of the petiole to the base of the leaf blade on the primary shoot. Secondary shoots are somewhat smaller depending on the age of the shoot. The petiole is approximately 3.8 mm in diameter just below the geniculum, and straight.

*Petiole wings.*—Petiole wings are approximately 1.2 cm to 1.4 cm in length and approximately 3.0 to 4.5 mm in width at their midpoint. The tips of the petiole wings are rounded. There is approximately 19 cm to 22 cm between the top of the wing and the base of the geniculum.

*Geniculum.*—The geniculum is approximately 25 mm to 26.5 mm in length, approximately 4.5 mm in diameter, and is often curved. The color is 146C. If grown in bright light, the exposed surface becomes anthocyanous. There is no space between the top of the geniculum and the base of the leaf blade. The geniculum is prominent.

*Veins.*—Veins are sunken, with the leaf blade slightly convex or flat between veins on the upper surface. The midrib protrudes from the upper surface of the leaf for approximately two-thirds the length of the leaf. Well defined primary veins on leaves radiate out from the juncture of the petiole and the leaf. Veins stand out prominently on the lower side. There are approximately 4–6 primary veins on the leaf. The junction of the petiole, midrib and primary veins often becomes anthocyanous when exposed to bright light.

*Lobes.*—The leaf has two rounded lobes which extend past the petiole. The distance from the petiole/leaf juncture to the highest point on the lobes is approximately 3.5 cm to 4.5 cm.

*Color.*—Upper surface: Closest to 139A but considerably darker and greener. Lower surface: 146B. Midrib, upper surface: 137A. Midrib, lower surface: 146C. Petiole: 146B, often darkened by anthocyanan pigment when exposed to bright light. Petiole wing: 146B-C.

Inflorescence

Immature: The spathe is tightly rolled aroung the spadix and extrudes from the petiole sheath. The spathe is fully open approximately when the pedicel is fully elongated, approximately 33 cm to 36 cm above the soil surface. The color of the pedicel is darker and greener than 152A with an anthocyanous cast.

Mature:

*Size.*—The flattened spathe is approximately 4.9 cm to 5.7 cm long and approximately 5 cm to 7 cm in width.

*Color.*—Fully open: Upper surface: 51C. Lower surface: 51D. Faded: Upper surface: 50D. The primary veins on the lobes of the spathe often darken to 144A with age. Lower surface: 49C.

*Arrangement.*—The spathe stands up on straight wiry pedicels and opens vertically above the leaves.

*Shape.*—The spathe is ovate with a cordate base and a cuspidate apice that is slightly hooked. It is distinctly cupped when first open and is approximately 4.9 cm to 5.7 cm in height, approximately 5.3 cm to 6.7 cm in width anad approximately 1.0 cm in depth. The spathe flattens somewhat as it ages.

*Flowering time.*—After approximately 6 months from a 20 week old liner for an untreated plant as illustrated in the photographs, and depending on season, approximately 2 to 4 blossoms will be present. Smaller blossoms may occur on less mature growth. First flowers (1 to 2) can be expected approximately 4–5 months after planting a 20 week old liner.

Reproductive organs

Spadix:

*Size.*—Approximately 3.9 cm to 4.6 cm in height and approximately 6 mm in width. There is approximately 5 mm to 8 mm between the junction of the pedicel and the spathe, and the lowermost flowers on the spadix.

*Color.*—When the spathe unrolls, the spadix is 179A at the tip, blending to 185D. The spadix gradually changes to 184A before senescing.

*Stamens.*—Anthers and filaments are not clearly visible.

*Pollen.*—158D in color.

*Pistil.*—Translucent 155C in color, protruding between the staminate flowers, firmly fixed to the main axil. The pistilate flowers extend approximately 0.2 mm beyond the staminate flowers.

Roots: White fleshy roots with fine laterals.

GENERAL OBSERVATION

Anthurium Bubble Gum has somewhat round and flat, medium pink spathes which are long lasting. The spathes are held upright, above and among the foliage. The leases are wide, leathery, very dark green, shiny and durable. The plant habit is branched, and compact. These combined characteristics make Bubble Gum a unique new cultivar.

I claim:

1. A new and distinct cultivar of Anthurium plant named Bubble Gum, as illustrated and described.

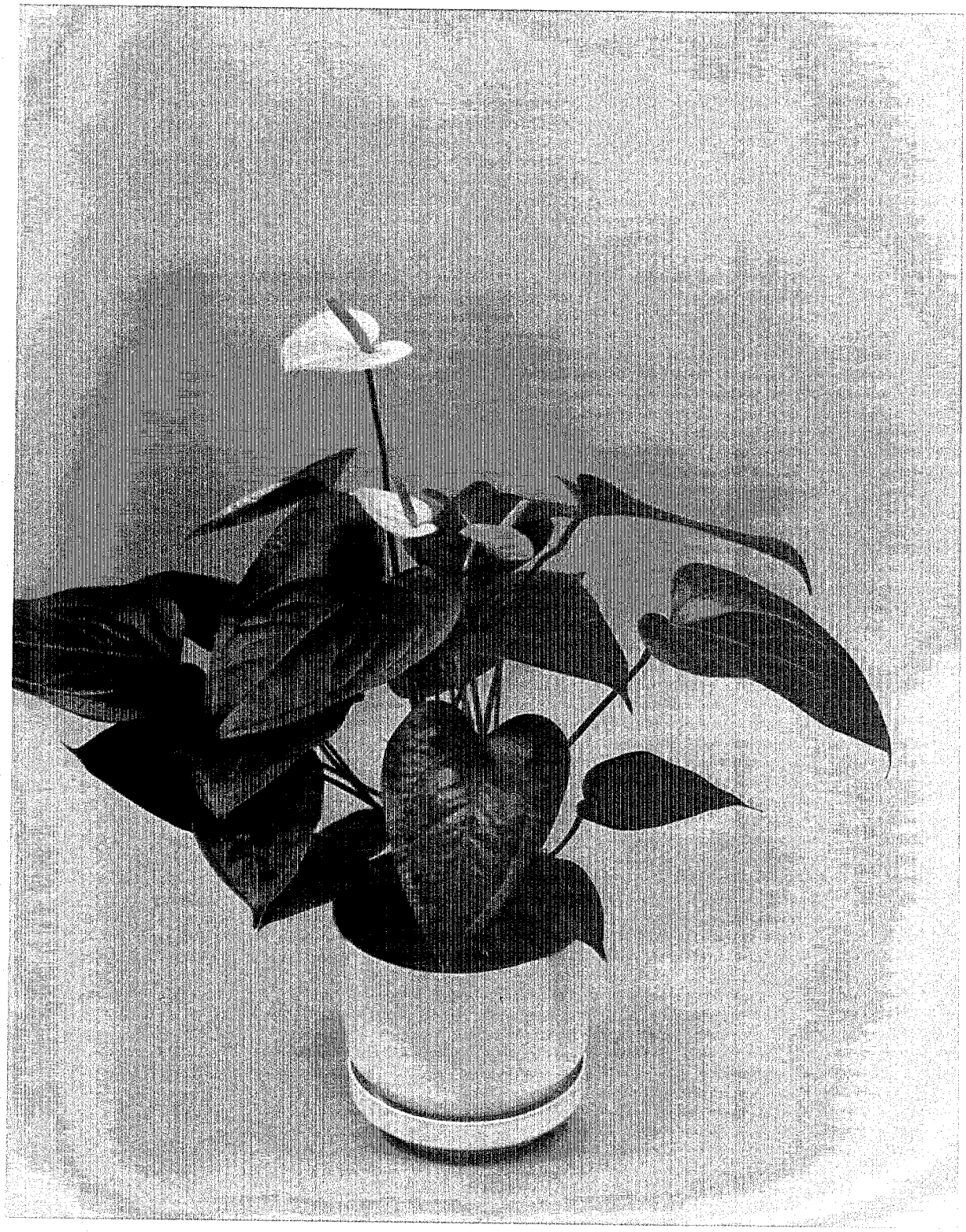

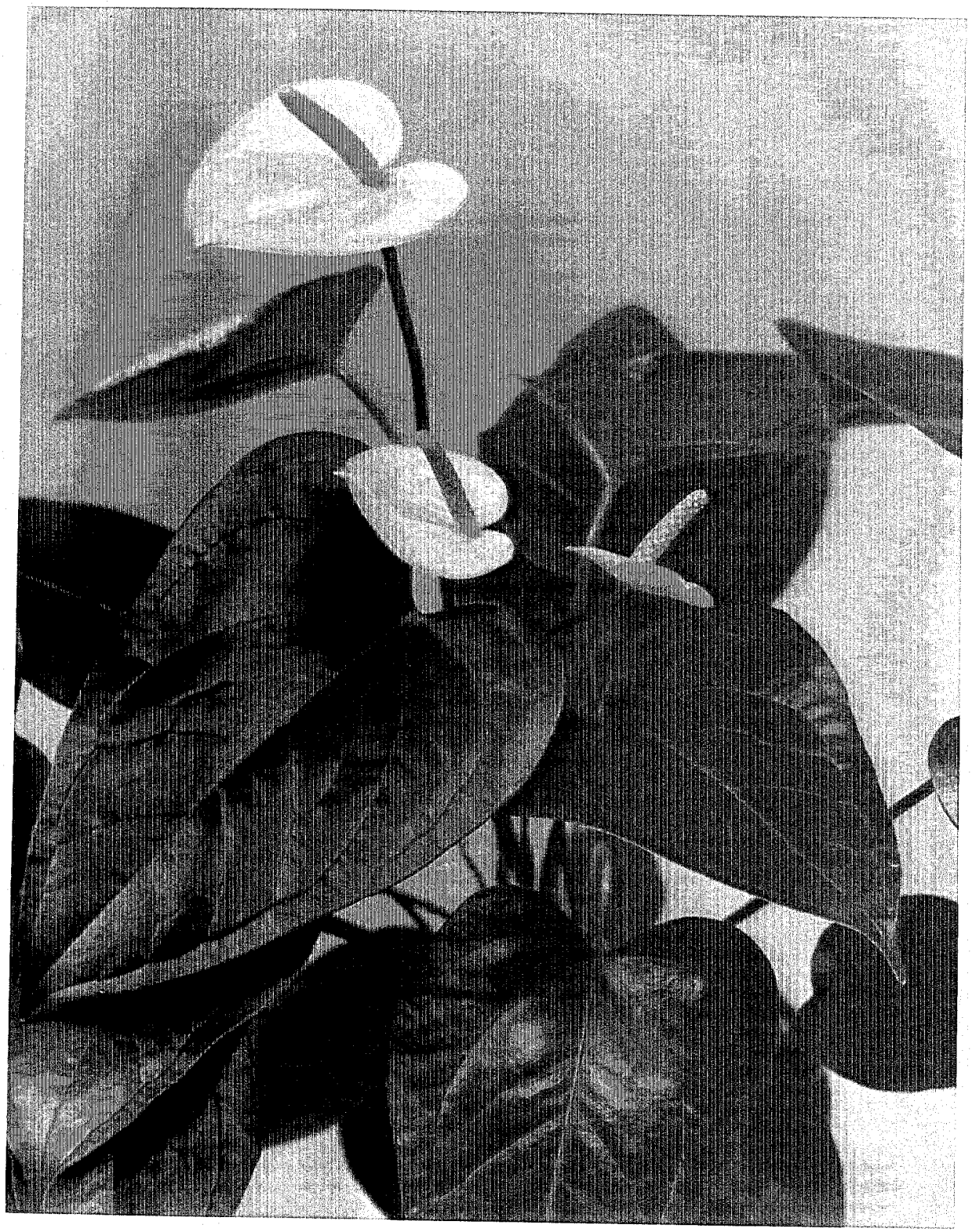

* * * * *